US00PP29824P3

(12) United States Plant Patent
Grosser

(10) Patent No.: US PP29,824 P3
(45) Date of Patent: Nov. 13, 2018

(54) SWEET ORANGE TREE NAMED 'FLORIDA EV2'

(50) Latin Name: *Citrus sinensis*
Varietal Denomination: Florida EV2

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 275 days.

(21) Appl. No.: 14/998,531

(22) Filed: Jan. 13, 2016

(65) Prior Publication Data

US 2017/0202122 P1 Jul. 13, 2017

(51) Int. Cl.
*A01H 5/08* (2018.01)

(52) U.S. Cl.
USPC ..... Plt./202
CPC ..... *A01H 5/0806* (2013.01)

(58) Field of Classification Search
USPC ..... Plt./202, 201
CPC ..... A01H 5/0806
See application file for complete search history.

(56) References Cited

U.S. PATENT DOCUMENTS

| | | | |
|---|---|---|---|
| PP21,535 | P2 | 11/2010 | Grosser et al. |
| PP26,087 | P3 | 11/2015 | Grosser |
| 2016/0120083 | P1 | 4/2016 | Grosser |
| 2016/0128252 | P1 | 5/2016 | Grosser |
| 2016/0128253 | P1 | 5/2016 | Grosser |

OTHER PUBLICATIONS

*Citrus,* (UF University of Florida IFAS 2017, 2 pages.) (http://research.ifas.ufl.edu/media/researchifasufledu/docs/pdf/Citrus.pdf).*
U.S. Appl. No. 14/998,502, filed Jan. 13, 2016, Grosser.
Grosser et al., "Protoplast fusion and citrus improvement," *Plant Breeding Reviews* 8:339-374, 1990.
Larkin et al., "Somaclonal variation—a novel source of variability from cell cultures for plant improvement" *Theoretical and Applied Genetics* 60:197-214, 1981.
Grosser et al., Somaclonal Variation in Sweet Orange: Practical Applications for Variety Improvement and Possible Causes. pp. 219-234. IN: Kahn, I.H. (Ed.). Citrus Genetics, Breeding and Biotechnology. CAB International, 2007.

* cited by examiner

*Primary Examiner* — Kent L Bell
(74) *Attorney, Agent, or Firm* — Dentons US LLP

(57) ABSTRACT

The new and distinct sweet orange tree described herein originated as a 'Valencia' somaclone tree regenerated from protoplasts isolated from an embryogenic suspension culture of standard 'Valencia' (*Citrus sinensis* L. Osbeck). 'Florida EV2' is a true 'Valencia' sweet orange with an altered maturity date that allows for harvest 8-12 weeks earlier than traditional 'Valencia' trees.

4 Drawing Sheets

Latin name of the genus and species of the plant claimed: *Citrus sinensis.*

Variety denomination: 'Florida EV2'.

BACKGROUND OF THE INVENTION

The present invention relates to a new and distinct variety of sweet orange named 'Florida EV2'. 'Florida EV2' originated as a 'Valencia' somaclone tree. In particular, 'Florida EV2' is a protoclone, regenerated from protoplasts isolated from an embryogenic suspension culture of standard 'Valencia' (*Citrus sinensis* L. Osbeck) in 1989. 'Florida EV2' is a separate protoclone, regenerated from the same experiment that generated 'SF14W-62' (U.S. Plant Pat. No. 21,535). Somaclonal variation is defined as variability in plants regenerated from tissue culture that is either induced or uncovered by a tissue culture process. Most somaclonal variation is negative, but if enough plants are examined, positive changes can usually be recovered. Somaclonal variation has been a primary source of genetic variation in sweet orange exploited in *citrus* improvement programs.

The first asexual reproduction of 'Florida EV2' involved grafting of the original tree to 'Carrizo' citrange rootstock and planting in Venus, Fla. in 1991. Thus, 'Florida EV2' is a true 'Valencia' sweet orange with an altered maturity date that allows for harvest 8-12 weeks earlier than traditional 'Valencia' trees.

SUMMARY OF THE INVENTION

The new and distinct variety of sweet orange bears fruit that ripens from December through January in central Florida. The trees usually bloom between early to late March in central Florida, depending on the season. 'Florida EV2' trees are similar in vigor to 'SF14W-62' and standard 'Valencia'. Second and third generation trees are less thorny than the sibling 'SF14W-62', and more like traditional 'Valencia' selections. Over the past two seasons, 'SF14W-62' has matured significantly earlier than the early-maturing 'SF14W-62'. 'Florida EV2' trees bear fruit that is typical of 'Valencia', although 'Florida EV2' fruit ripen 8-12 weeks earlier than standard 'Valencia' trees, based on the brix/acid ratio (Tables 1-3). Juice data from the original tree did not show that 'Florida EV2' matures earlier than 'SF14W-62', however, fruit on propagated trees have exhibited earlier maturity over the past two seasons. Juice quality of 'Florida EV2' is typical of 'Valencia' in sugar and acid content, color, and flavor. The fruit are juicy and difficult to peel. Fruit are slightly more seedy than standard 'Valencia', with 7-8 seeds per fruit (standard 'Valencia' has 4-5 seeds per fruit). The tree appears to be at least as productive as standard 'Valencia' trees.

The following are the most outstanding and distinguishing characteristics of 'Florida EV2' when grown under normal horticultural practices in Florida. (1) Fruit ripen 8-12 weeks earlier than standard 'Valencia'; and (2) Fruit have excellent juice quality during the early 'Hamlin' harvest period.

'Florida EV2' produces standard Valencia-type sweet orange fruit, but with a significantly earlier fruit maturation date (8-12 weeks) than standard 'Valencia' (Tables 1-3). In Florida, fruit can generally be harvested from December through January, depending on environmental conditions. As shown in Table 3, for the 2014-2015 juice season, fruit from 6-year-old trees on rough lemon rootstock produced juice with a brix/acid ratio of 16, whereas 'Hamlin' fruit from the same block produced juice with a brix/acid percent ratio of 12. Juice quality from fruit of 'Florida EV2' was of much higher quality than that of 'Hamlin', and more similar to that of standard 'Valencia', the highest quality juice orange currently available. The present 'Florida EV2' selection therefore provides the processing industry with an opportunity to replace 'Hamlin', which is currently the standard early-maturing cultivar in the Florida juice industry. Replacing 'Hamlin' with new Valencia types such as 'Florida EV2' has the potential to significantly improve the flavor and color of NFC (Not From Concentrate) orange juice. Better quality juice may help offset declining orange juice consumption in the United States. In the event of January or February freeze-mandated harvests, this would allow for grade A juice recovery without the economic loss encountered with standard 'Valencia' fruit that is not fully mature at the time of harvest. 'Florida EV2' has a maturity date similar to that of Valencia somaclone 'Florida EV1' (Co-pending U.S. Plant patent application Ser. No. 14/998,502), but appears to be slightly later. Both trees have been significantly earlier than 'SF14W-62' (U.S. Plant Pat. No. 21,535) the past two seasons.

TABLE 1

Original tree data suggesting early maturity for Valencia somaclone 'Florida EV2' (Data from Southern Farms Trial, Venus,Florida). Trial no longer exists.

| Date | Selection | Brix | Acid | Ratio | Lbs. solids | Juice Color* |
|---|---|---|---|---|---|---|
| Jan. 31, 2000 | Somaclone 'Florida EV2' | 11.32 | .87 | 13.01 | 5.58 | 37.4 |
| | 'Valencia' Control | 11.41 | 1.14 | 10.01 | 5.94 | 37.1 |
| Feb. 06, 2001 | Somaclone 'Florida EV2' | 12.26 | .92 | 13.33 | 6.17 | 36.8 |
| | 'Valencia' Control | 11.52 | 1.00 | 11.52 | 5.87 | 35.9 |

TABLE 2

Juice data from 5-year old trees on rough lemon rootstock, Alligator Grove, St. Cloud, Florida.

| ANALYSIS DATE | SAMPLE ID | BRIX COR. | ACID % | RATIO | pH |
|---|---|---|---|---|---|
| Jan. 14, 2014 | 'Vernia'/Rough Lemon | 11.29 | 0.73 | 15.47 | 3.75 |
| Jan. 14, 2014 | 'Florida EV2'/Rough Lemon | 11.68 | 0.59 | 19.80 | 4.13 |
| Jan. 14, 2014 | 'SF14W-62'/Rough Lemon | 10.27 | 0.72 | 14.26 | 3.86 |
| Jan. 14, 2014 | 'Valencia'/Rough Lemon | 9.22 | 0.80 | 11.53 | 3.66 |
| Jan. 14, 2014 | 'OLL-8'/Rough Lemon | 10.78 | 1.05 | 10.27 | 3.52 |
| Jan. 14, 2014 | 'Florida EV1'/Rough Lemon | 10.32 | 0.51 | 20.24 | 4.14 |

| ANALYSIS DATE | Juice Color* | OIL % | SINKING PULP | VIT. C (mg/100ml) | Limonin ppm |
|---|---|---|---|---|---|
| Jan. 14, 2014 | 36.22 | 0.018 | 16.0 | 50.38 | 23.1 |
| Jan. 14, 2014 | 35.14 | 0.035 | 18.0 | 47.49 | 5.8 |
| Jan. 14, 2014 | 35.83 | 0.026 | 14.0 | 47.09 | 9.0 |
| Jan. 14, 2014 | 35.33 | 0.012 | 12.0 | 43.71 | 11.1 |
| Jan. 14, 2014 | 36.77 | 0.015 | 13.0 | 50.51 | 10.7 |
| Jan. 14, 2014 | 35.00 | 0.029 | 16.0 | 46.27 | 4.2 |

TABLE 3

Juice data from 6-year-old trees on rough lemon rootstock, Alligator Grove, St. Cloud, Florida. Pilot-plant data from samples run on Dec. 10, 2014.

| Sample | Variety | Lbs. Juice Per Box | Acid | Total Brix | Ratio | Fruit Ct | Lbs. Solids Per Box | Juice color* |
|---|---|---|---|---|---|---|---|---|
| 1 | 'Vernia' | 53.906 | 0.87 | 11.04 | 12.69 | 78 | 5.95 | 35.3 |
| 2 | 'Florida EV1' | 50.913 | 0.71 | 11.30 | 15.92 | 61 | 5.75 | 36 |
| 3 | 'Hamlin' | 52.914 | 0.94 | 11.17 | 11.88 | 64 | 5.91 | 34.5 |
| 4 | 'SF14W-62' | 50.728 | 0.84 | 9.87 | 11.75 | 55 | 5.01 | 35.7 |
| 5 | 'Florida EV2' | 50.299 | 0.67 | 11.06 | 16.51 | 63 | 5.56 | 36 |
| 6 | 'Valencia' | 53.443 | 0.98 | 9.53 | 9.72 | 58 | 5.09 | 35.4 |

*Juice color, also referred to as juice color number, is an industry standard measurement of citrus juice color that can be obtained using a HunterLab Model D45 Citrus Colorimeter for which the Citrus Red (CR) and Citrus Yellow (CY) has been calibrated with USDA orange juice standard color tube No 4; USDA grade "A" orange juice requires a juice color number of at least 36. Juice color number is calculated using the following formula: 22.510 + (0.165) * CR + (0.111) * CY.

BRIEF DESCRIPTION OF THE DRAWINGS

'Florida EV2' is illustrated by the accompanying photographs, which show the tree's form, foliage, and fruit. The colors shown are as true as can be reasonably obtained by conventional photographic procedures. The photographs are of a tree approximately 6 years old.

FIG. 1—Shows a close-up of the mature 'Florida EV2' fruit with the rind, and a cross-sectional view of the fruit when cut in the center.

FIG. 2—Shows the overall mature plant growth habit in December.

FIG. 3—Shows a close-up of the mature fruit and heavy cropping on tree.

FIG. 4—Shows a close up of a whole, mature fruit.

DETAILED BOTANICAL DESCRIPTION

Figure 1:
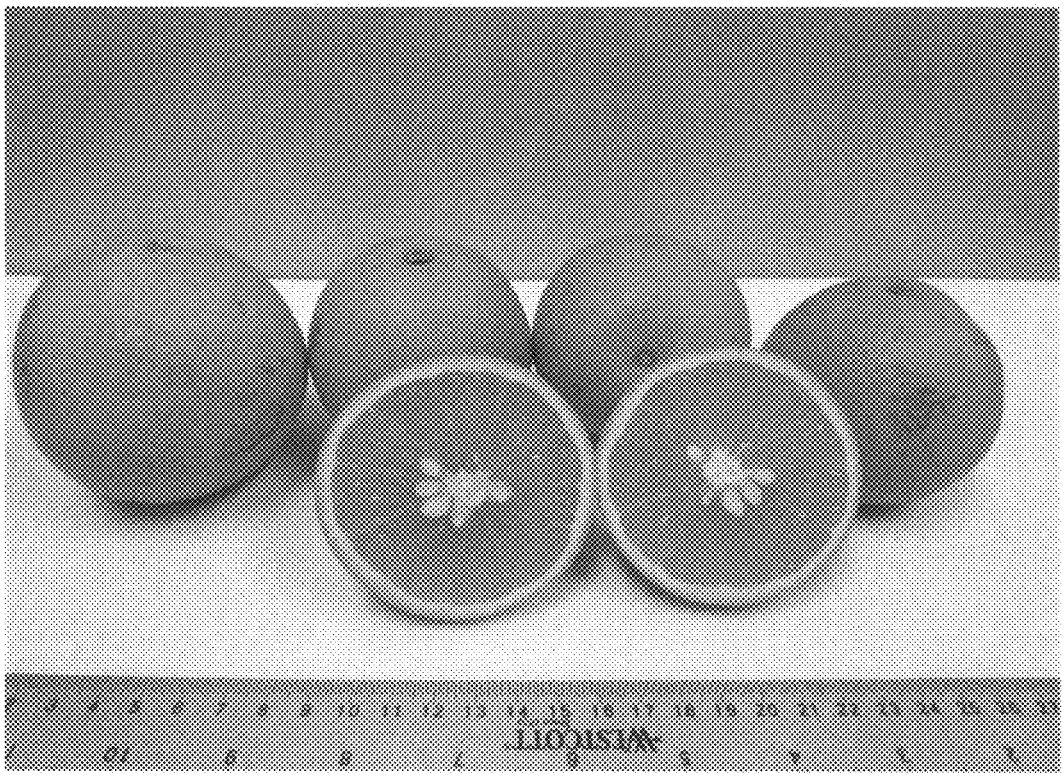
FIGS. 1-4 were taken during the early winter (December 2014) from the same tree.
Figure 2:
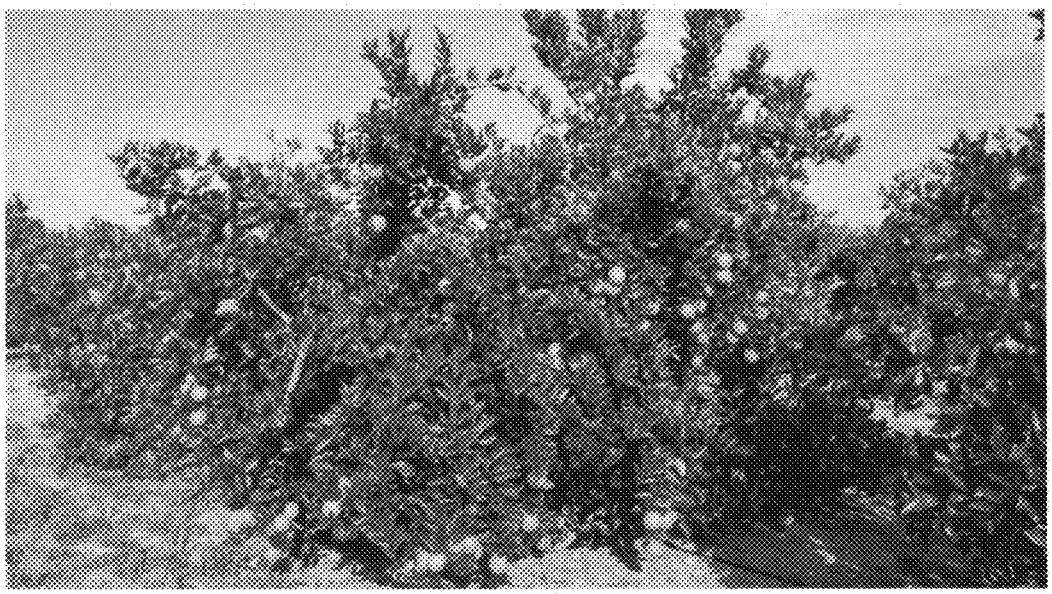
Figure 3:
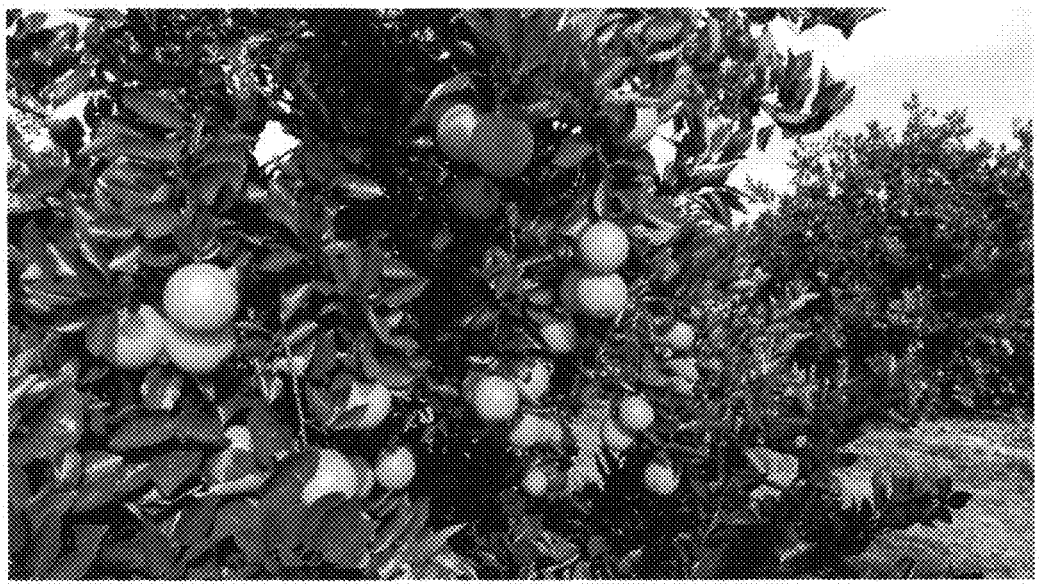
Figure 4:
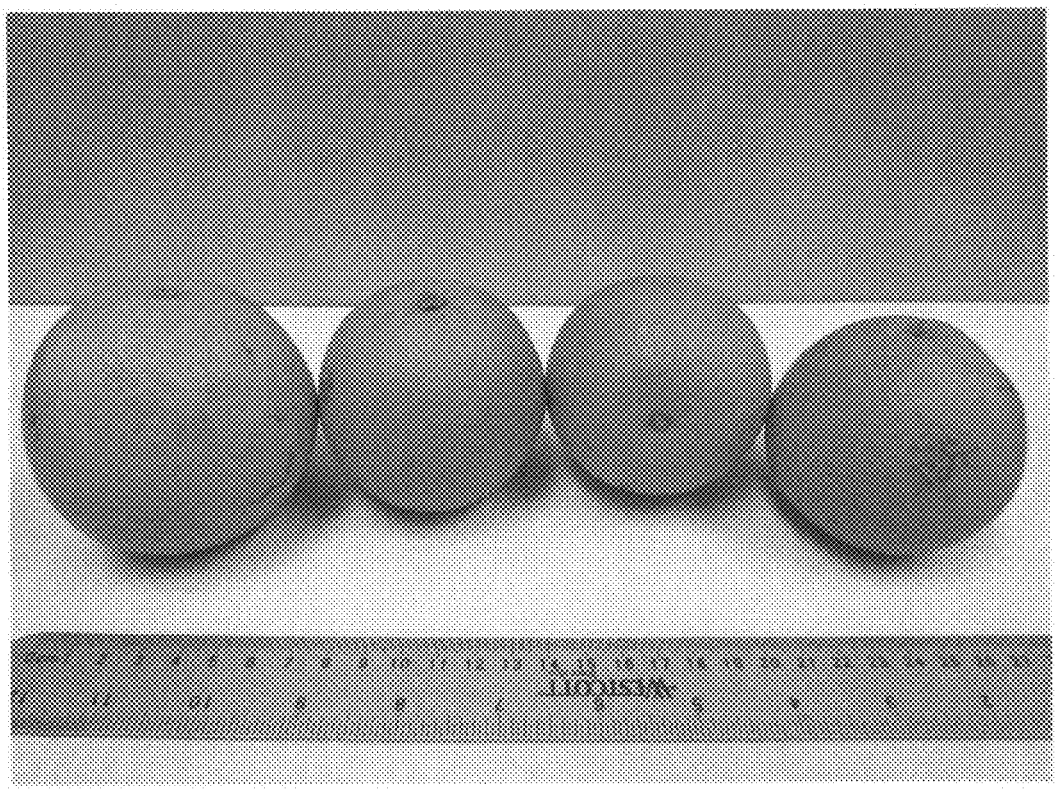

Phenotypic Description of *Citrus Sinensis* 'Florida EV2'

The following detailed description sets forth the distinctive characteristics of 'Florida EV2'. The present botanical description is that of 'Florida EV2' grown as a 6-year-old tree growing on rough lemon (rootstock) in St. Cloud, Fla. The colors (except those in common terms) are described from The R.H.S. Colour Chart published by The Royal Horticultural Society in London (second edition), in association with the Flower Council of Holland.

Classification:

*Botanical.*—*Citrus sinensis* (putative).

*Common name.*—Sweet orange.

Parentage:

*Female parent.*—'Valencia' sweet orange (unpatented).

*Male parent.*—N/A.

Tree:

*Ploidy.*—Diploid.

*Size.*—Medium large.

*Height.*—3.6 meters.

*Tree spread.*—4.0 to 4.5 meters.

*Vigor.*—Similar to standard 'Valencia'.

*Density.*—Canopies are quite dense.

*Form.*—The tree is round shaped with both lateral and upright branches growing toward low to medium angles. Branches with multiple fruit exhibit drooping.

*Growth habit.*—Both upright and lateral growth.

Trunk and branches:

*Trunk diameter.*—13.5 cm at 30 cm above the ground on a 6-year-old tree.

*Trunk texture.*—Smooth.

*Trunk bark color.*—RHS 198A (greyed-green); irregularly striated with RHS 147A (yellow-green).

*Crotch angle.*—First crotch forms a 40- to 45-degree angle, middle crotch forms a 30-degree angle.

*Branch length.*—Branches reach 4 meters from the first crotch to the tip of the branch.

*Branch texture.*—Relatively smooth, occasionally with thorns or spines.

*Branch color* (*shoots from previous flush, hardened, and* 4 *to* 5 *mm in diameter*).—RHS N137A (green).

Leaves:

*Size* (*lamina average*).—Length: 109.8 mm. Width: 63.7 mm. L/W ratio: 1.72.

*Thickness.*—Regular and average compare to commercial sweet orange.

*Type.*—Simple.

*Shape.*—Elliptical.

*Apex.*—Retuse.

*Base.*—Acute to sub-obtuse.

*Margin.*—Entire and slightly undulate.

*Surface.*—Upper surface: Glabrous. Lower surface: Medium veins that are pinnately netted.

*Color.*—Upper surface (adaxial): RHS N137A (green). Lower surface (abaxial): RHS 144B (yellow-green).

*Petiole.*—Shape: Brevipetiolate (shorter than leaf lamina); junction between petiole and lamina is articulate. Width (petiole wing): Narrow. Shape (petiole wing): Obovate. Length: 18.9 to 21.1 mm. Width: 5.0 to 5.1 mm. Color: RHS N137A (green).

Flowers and flower buds:

*Type.*—Hermaphroditic.

*Bearing.*—Flowers grow from leaf axillaries and leaf terminals singly and in small clusters; single flowers mostly grow from leaf axillaries; each flower branch consists of 7-16 flowers.

*Flower diameter.*—Fully open flower has an average diameter of 36.8 to 37.2 mm.

*Flower depth.*—Typical flower has an average depth of 14.9 mm.

*Flower blooming period.*—First bloom observed Feb. 28, 2015. Full bloom observed Mar. 7, 2015.

*Flower bud size.*—Length: Initial visible flower bud is 2.2 mm in length; mature flower bud is 17.2 mm in length. Diameter: Initial visible flower bud is 2.3 mm in diameter; mature flower bud is 6.0 mm in diameter. Shape: Initial visible flower bud has a round ball shape; mature flower bud has an elongated olive shape.

*Color.*—RHS143B (green) for initial visible flower bud; RHS155B (white) for mature flower bud, with RHS150D (yellow) spots distributed at tip of the flower bud.

*Flower petals.*—Shape: Flat, spatula-shaped. Apex shape: Smooth, acute-shaped. Base shape: Even obtuse. Color: Upper surface RHS155B (white); lower surface RHS155B (white), with RHS150D (yellow-green) spots distributed toward the petal apex. Margin: Smooth.

*Flower sepal.*—Number: 5 per flower. Shape: Delta-shaped with acute angle at apex, some sepals with splitting di-triangle points. Length: 4.3 mm. Width: 4.0 mm. Apex shape: Triangle-shaped, some with di-triangle points. Margin: Smooth. Color: Upper surface RHS150D (yellow-green); lower surface RHS149D (yellow-green).

*Fragrance.*—Fragrant.

*Flower pedicel.*—Length: 6.8 to 7.1 mm. Diameter: 1.0 to 1.2 mm. Color: RHS144D (yellow-green).

Reproductive organs:

*Fertility.*—Appears self-fertile.

*Stamen length.*—13 to 13.2 mm.

*Anther length.*—2.8 mm.

*Anther width.*—1.2 to 1.3 mm.

*Anther color.*—RHS11B (yellow).

*Anther filament length.*—10.7 to 10.9 mm.

*Pollen amount.*—Abundant/Moderate amount.

*Pollen color* (*general*).—RHS12A (bright-yellow).

*Pistil number.*—1.

*Pistil length.*—12 to 12.2 mm.

*Pistil color.*—RHS 4C (yellow).

*Style length.*—8 mm.

*Style diameter.*—1.4 to 1.5 mm.

*Style color.*—RHS149D (yellow-green).

*Ovary shape.*—Oval-shaped.

*Ovary diameter.*—3.1 mm.

*Ovary color.*—RHS 144D (yellow-green).

Fruit:

*Size.*—Uniform.

*Tall.*—67.5 to 78.2 mm on average.

*Width.*—72.9 to 80.5 mm on average.

*Average weight* (*per individual fruit*).—206.2 grams.

*Shape.*—Round.

*Shape* (*cross-section*).—Round.

*Apex.*—Truncated.

*Apex cavity diameter*.—N/A.

*Base cavity diameter*.—6.4 to 7.5 mm.

*Base*.—Not necked.

*Harvesting*.—First harvest around Dec. 10, 2014 (based on season and rootstock); fruit hold on the tree with good quality through January.

*Fruit stem* (*short stem connecting the fruit*).—Length: 9.6 mm. Diameter: 3.8 mm. Color: RHS 198D (greyed-green) with RHS 137A (green) strip.

*Fruit core*.—Size: 7.0 mm to 11.0 mm. Color: RHS NN155-B (white).

Rind:

*Adherence*.—Adherence between albedo (mesocarp) and flesh (endocarp) is strong and evenly distributed from base to apex.

*Thickness*.—3.4 to 5.0 mm on average.

*Texture*.—Smooth.

*Color*.—Flavedo (epicarp): Ranges between RHS 15A (yellow-orange) to RHS 17A (yellow-orange). Albedo (mesocarp): RHS 18B (yellow-orange).

*Stylar end*.—Closed.

*Rind oil cell density*.—248 oil cells/square cm.

Flesh:

*Number of segments*.—Average between 11 and 12 segments per fruit.

*Segment walls*.—Medium soft with sufficient strength to maintain integrity as separated.

*Juice*.—Abundant.

*Color*.—Uniformly RHS 21A (yellow-orange).

*Texture*.—Medium soft.

*Vesicles*.—Length: Arranged from 16.7 to 21 mm on average. Diameter (thickness): 2.5 to 3.4 mm on average.

*Eating quality as of Dec.* 8, 2014.—Soluble solids (average): 11.1 Brix. Acidity (average): 0.67%. Ratio: 16.5.

Seeds:

*Type*.—Polyembryonic.

*Number*.—Ranges from 7 to 8. Occasionally some fruit contain less than 7 seeds.

*Shape*.—Seed shapes are not uniform. Normal seeds are mostly ventricose/swollen-shaped and clavate, club-shaped.

*Size*.—Length: 14 to 14.5 mm. Width: 7.0 to 8.5 mm.

*Seed coat color*.—Outer Surface: RHS NN155A (white) and wrinkled. Inner surface: RHS 165B (greyed-orange).

*Cotyledon color*.—RHS 157D (green-white).

Disease/insect resistance: No apparent differences from standard 'Valencia'.

What is claimed is:

1. A new and distinct cultivar of sweet orange tree as illustrated and described herein.

* * * * *